United States Patent
Sakoda et al.

(10) Patent No.: US 8,952,338 B2
(45) Date of Patent: Feb. 10, 2015

(54) CRYSTALLINE QUALITY EVALUATION APPARATUS FOR THIN-FILM SEMICONDUCTORS, USING μ-PCD TECHNIQUE

(75) Inventors: Naokazu Sakoda, Kobe (JP); Hiroyuki Takamatsu, Kobe (JP); Masahiro Inui, Kobe (JP); Futoshi Ojima, Kobe (JP)

(73) Assignees: Kobe Steel, Ltd. (JP); Kobelco Research Institute Inc. (JP)

( * ) Notice: Subject to any disclaimer, the term of this patent is extended or adjusted under 35 U.S.C. 154(b) by 0 days.

(21) Appl. No.: 13/819,288

(22) PCT Filed: Sep. 1, 2011

(86) PCT No.: PCT/JP2011/004911
§ 371 (c)(1),
(2), (4) Date: Feb. 26, 2013

(87) PCT Pub. No.: WO2012/039099
PCT Pub. Date: Mar. 29, 2012

(65) Prior Publication Data
US 2013/0153778 A1    Jun. 20, 2013

(30) Foreign Application Priority Data

Sep. 22, 2010   (JP) .................... 2010-211524

(51) Int. Cl.
*G01T 1/16*    (2006.01)
*G01N 21/63*   (2006.01)
(Continued)

(52) U.S. Cl.
CPC   *G01T 1/16* (2013.01); *G01N 21/63* (2013.01); *H01L 22/12* (2013.01); *G01N 21/8422* (2013.01); *G01N 22/00* (2013.01)
USPC ........................................................ 250/393

(58) Field of Classification Search
CPC .......... H01L 21/302; H01L 22/12; G01T 1/16
USPC ........................................................ 250/393
See application file for complete search history.

(56) References Cited

U.S. PATENT DOCUMENTS 5,580,828 A * 12/1996 Ferenczi et al. ................ 438/16
6,653,850 B2 * 11/2003 Pavelka ..................... 324/754.23
(Continued)

FOREIGN PATENT DOCUMENTS

JP    2006-196621    7/2006
JP    2007-48959     2/2007
(Continued)

OTHER PUBLICATIONS

Office Action from Japanese Patent Office for corresponding Japanese Patent Application 2010-211524 issued on Jun. 25, 2013.
(Continued)

*Primary Examiner* — Marcus Taningco
(74) *Attorney, Agent, or Firm* — Studebaker & Brackett PC; Donald R. Studebaker

(57) ABSTRACT

The present invention provides a crystalline quality evaluation apparatus (1) and a crystalline quality evaluation method for thin-film semiconductors, which are designed to evaluate crystalline quality of a sample (2) of a thin-film semiconductor (2a) by emitting excitation light and an electromagnetic wave to irradiate a measurement site of the sample (2), and detecting an intensity of a reflected electromagnetic wave from the sample (2). In the present invention, the thin-film semiconductor (2a) of the sample (2) is formed on an electrically conductive film (2b), and a dielectric (3) transparent to the excitation light is additionally disposed between the sample (2) and a waveguide (13) for emitting the electromagnetic wave therefrom. Thus, the thin-film semiconductor crystalline quality evaluation apparatus (1) and method configured in this manner make it possible to evaluate the crystalline quality even in the above situation where the electrically conductive film (2b) is formed under the semiconductor thin-film (2a).

6 Claims, 6 Drawing Sheets

(51) Int. Cl.
*H01L 21/66* (2006.01)
*G01N 21/84* (2006.01)
*G01N 22/00* (2006.01)

(56) References Cited

U.S. PATENT DOCUMENTS

| | | | |
|---|---|---|---|
| 6,693,286 B2 * | 2/2004 | Hasegawa et al. | 250/458.1 |
| 2007/0187875 A1 | 8/2007 | Terasaki et al. | |
| 2009/0115029 A1 * | 5/2009 | Koyama et al. | 257/632 |
| 2009/0152239 A1 | 6/2009 | Terasaki et al. | |
| 2009/0152753 A1 | 6/2009 | Terasaki et al. | |
| 2011/0278259 A1 | 11/2011 | Terasaki et al. | |
| 2011/0294256 A1 | 12/2011 | Kubo et al. | |

FOREIGN PATENT DOCUMENTS

| | | |
|---|---|---|
| JP | 2007-103915 | 4/2007 |
| JP | 2008-051719 | 3/2008 |
| JP | 2010-043906 | 2/2010 |
| JP | 2011-069662 | 4/2011 |
| WO | WO 2010/074283 A1 | 7/2010 |

OTHER PUBLICATIONS

International Search Report issued from the International Bureau in the corresponding International Application No. PCT/JP2011/004911, mailed Nov. 15, 2011.

* cited by examiner

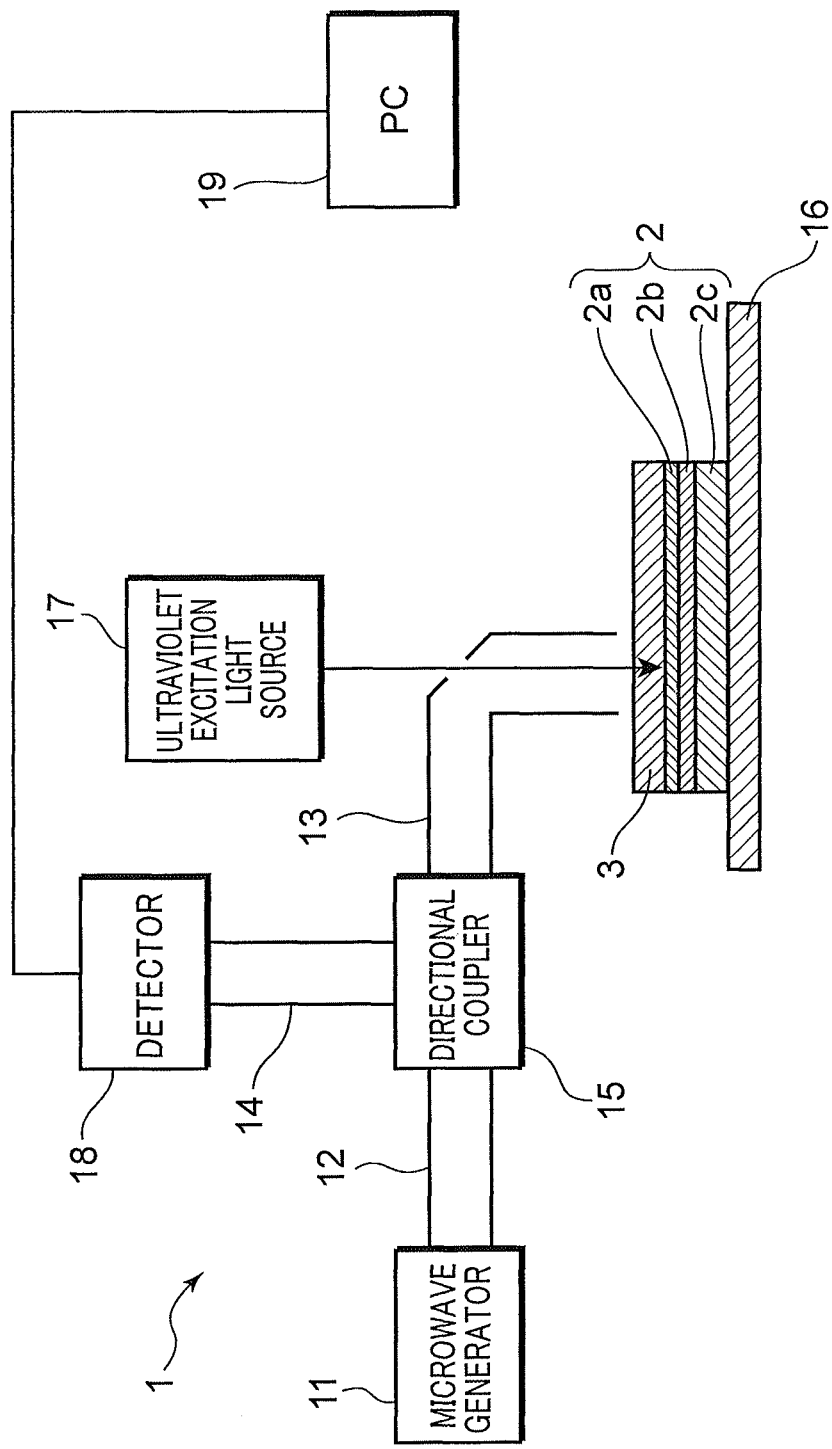

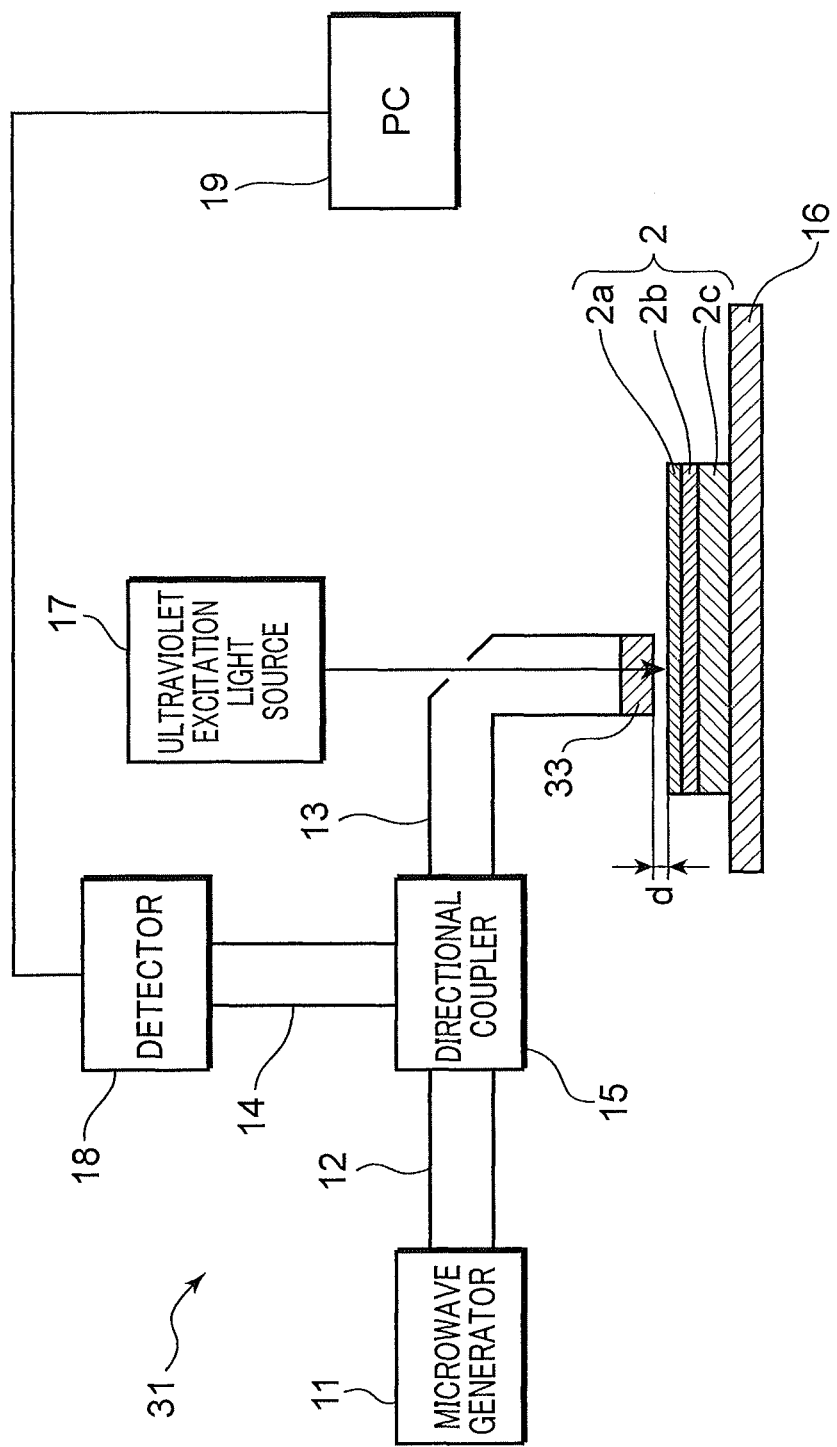

CRYSTALLINE QUALITY EVALUATION APPARATUS FOR THIN-FILM SEMICONDUCTORS, USING μ-PCD TECHNIQUE

TECHNICAL FIELD

The present invention relates to a crystalline quality evaluation apparatus and method for thin-film semiconductors, and particularly to a thin-film semiconductor crystalline quality evaluation apparatus and method suitably implementable for evaluating crystalline quality of a semiconductor thin-film such as a silicon thin-film, using a microwave photoconductivity decay technique (hereinafter referred to as "μ-PCD technique").

BACKGROUND ART

Late years, the development of a solar cell using a semiconductor thin-film such as a silicon thin-film has been actively carried out. Heretofore, in the field of semiconductors, the μ-PCD technique has been frequently employed as a noncontact and nondestructive evaluation method for the evaluation of impurity contamination and defect (for example, a silicon wafer carrier lifetime measuring method disclosed in the following Patent Document 1).

In the μ-PCD technique, an electromagnetic wave is emitted to irradiate a semiconductor sample, thereby causing free electrons in the semiconductor sample to move (migrate) according to an electric field of the electromagnetic wave. A state of the movement is influenced by the presence of impurities, defects or the like in the semiconductor sample. Thus, an intensity of a reflected wave of the electromagnetic wave emitted to irradiate the semiconductor sample (a change in intensity of the reflected wave as compared to the emitted wave) can be treated as an index of crystalline quality of the semiconductor sample. The μ-PCD technique is designed to evaluate crystalline quality of a semiconductor sample by means of the above mechanism. In addition, the μ-PCD technique has an advantage of being able to detect (measure) the reflected wave within a significantly short period of time, in a nondestructive and noncontact manner.

However, a wavelength of an electromagnetic wave (microwave) is as long as several millimeters or more, which poses a problem of failing to evaluate crystalline quality in a small area. Moreover, in cases where a semiconductor sample has a thin thickness (is a thin-film sample), for example, when the semiconductor sample is a polycrystalline silicon sample having a thickness of about several to several ten nm, or a monocrystalline silicon sample having a thickness of several μm or less, a change in intensity of an electromagnetic wave when comparing a reflected wave to an emitted wave (a change in intensity of the reflected wave due to crystalline quality of the semiconductor sample) becomes extremely small, which poses a problem of failing to ensure sufficient measurement sensitivity, i.e., measurement accuracy. On the other hand, if an intensity of excitation light is excessively increased so as to enhance the measurement sensitivity, the sample is likely to be damaged, and a light source of the excitation light involves an increase in cost.

Therefore, the inventors of this application proposed a technique disclosed in the following Patent Document 2. This conventional technique is designed to emit excitation light having energy equal to or greater than a band gap of the above thin-film sample, to irradiate a small area of the thin-film sample, in a converging manner, thereby generating photo-excited carriers in the small area of the sample, wherein a movement of the photo-excited carriers according to an electric field of an electromagnetic wave is used, instead of the movement of free electrons. In this case, the intensity of the reflected wave which changes in response to irradiation with the excitation light is detected, so that it becomes possible to evaluate such a thin-film sample, using the detected intensity as an index representing crystalline quality in a small area (excitation light irradiation area) of the sample. Further, in this conventional technique, although a change in intensity of the reflected light is small because the excitation light irradiation area is small, and thereby becomes more susceptible to noise, an unwanted frequency component (noise) is removed by forming the excitation light as light intensity-modulated in predetermined periods and extracting a component synchronous with the intensity-modulation of the excitation light, from the detected intensity of the reflected light.

The technique disclosed in the Patent Document 2 is excellent in terms of capability to evaluate crystalline quality in a small area of a TFT or the like. However, in the conventional μ-PCD technique, in a situation where there is an electrically conductive film immediately below a semiconductor thin-film as an evaluation target, a sufficient electric field intensity cannot be obtained in the semiconductor thin-film, and an interaction of the electric field with photo-excited carriers becomes weak, which poses a problem of great difficulty in performing the measurement. Specifically, in the case where particularly low-cost amorphous silicon or microcrystalline silicon is used in a solar cell, a back (bottom) electrode is formed on a glass substrate, and then a semiconductor thin-film is formed thereon, so that the bottom electrode becomes the electrically conductive film. The same problem occurs in the filed of FPDs (Flat-Panel Displays) employing a bottom gate structure.

LIST OF PRIOR ART DOCUMENTS

Patent Documents

Patent Document 1: JP 2007-48959A
Patent Document 2: JP 2008-51719A

SUMMARY OF THE INVENTION

The present invention has been made in view of the above circumstances, and an object thereof is to provide a thin-film semiconductor crystalline quality evaluation apparatus and method capable of evaluating crystalline quality of a semiconductor thin-film using a μ-PCD technique, even in a situation where an electrically conductive film is formed under the semiconductor thin-film.

The present invention provides a crystalline quality evaluation apparatus and a crystalline quality evaluation method for thin-film semiconductors, which are designed to evaluate crystalline quality of a sample of a thin-film semiconductor by emitting excitation light and an electromagnetic wave to irradiate a measurement site of the sample, and detecting an intensity of a reflected electromagnetic wave from the sample. In the present invention, the thin-film semiconductor of the sample is formed on an electrically conductive film, and a dielectric transparent to the excitation light is additionally disposed between the sample and a section for emitting the electromagnetic wave.

Thus, the thin-film semiconductor crystalline quality evaluation apparatus and method configured in this manner make it possible to evaluate the crystalline quality even in the above situation where the electrically conductive film is formed under the semiconductor thin-film.

The above and other objects, features and advantages of the present invention will be apparent from the following detailed description and the accompanying drawings.

BRIEF DESCRIPTION OF THE DRAWINGS

FIG. 1 is a block diagram illustrating a configuration of a thin-film semiconductor crystalline quality evaluation apparatus according to a first embodiment of the present invention.

FIG. 6 is a block diagram illustrating a configuration of a thin-film semiconductor crystalline quality evaluation apparatus according to a second embodiment of the present invention.

DESCRIPTION OF EMBODIMENTS

Figure 2A:
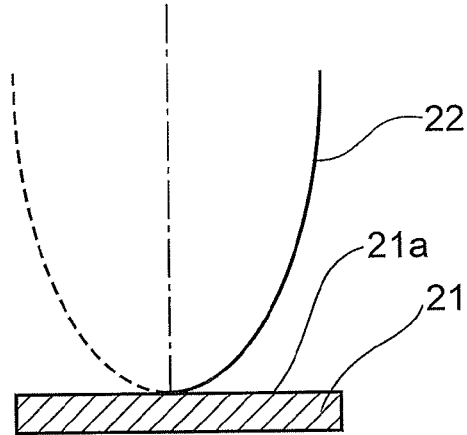
FIG. 2 is a diagram illustrating a state of a standing wave when a microwave is emitted to irradiate a metal stage.

An embodiment of the present invention will now be described based on the drawings. In the figures, two or more elements or components assigned with the same reference numeral or code mean that they are the same element or component, and their duplicated description will be omitted on a case-by-case basis.

(First Embodiment)

FIG. 1 is a block diagram illustrating a configuration of a thin-film semiconductor crystalline quality evaluation apparatus 1 according to a first embodiment of the present invention. The evaluation apparatus 1 is basically designed to evaluate crystalline quality of a semiconductor using the aforementioned μ-PCD technique, wherein it can evaluate a sample 2 under a condition that a dielectric 3 is superimposed on the sample 2, even in a situation where a laminate of a glass substrate (thickness: several mm) 2c and an electrically conductive film 2b and a thin-film semiconductor 2a (thickness: about several μm) formed on the glass substrate 2c is used as the sample 2, as described later. For example, such a sample 2 includes a solar cell formed with a bottom electrode, and an FPD employing a bottom gate structure. The evaluation apparatus 1 can also evaluate a semiconductor wafer or the like in a conventional manner without interposing the dielectric 3.

For example, as illustrated in FIG. 1, the evaluation apparatus 1 comprises a microwave generator 11, a plurality of waveguides 12, 13, 14, a directional coupler 15, a stage 16, an ultraviolet excitation light source 17, a detector 18, a personal computer 19, and the dielectric 3.

A microwave emitted from the microwave generator 11 which is one example of an electromagnetic wave emitting section is propagated from the waveguide 12 through the directional coupler 15 and the waveguide 13, and emitted to irradiate a measurement site of the sample on the stage 16. The microwave emitted from a distal end of the waveguide 13 to irradiate the sample is reflected by a surface of the sample, and entered into the waveguide 13 again. Ultraviolet excitation light having energy equal to or greater than a band gap of the semiconductor of the sample is emitted from the ultraviolet excitation light source 17 which is one example of an excitation light emitting section, to irradiate an area narrower than an irradiation area with the microwave. During the irradiation with the ultraviolet excitation light, photo-excited carriers are generated in the semiconductor, so that a microwave reflection rate is temporarily increased. The reflected microwave is guided returningly from the waveguide 13 to the waveguide 14 via the directional coupler 15, and detected by the detector 18 which is one example of a detection section. A detection signal from the detector 18 is transmitted to the personal computer 19 which is one example of an evaluation section.

In this way, the photo-excited carriers generated in the semiconductor by the irradiation with the ultraviolet excitation light move (migrate) according to an electric field of the electromagnetic wave (microwave), and a state of the movement is influenced by the presence of impurities, defects or the like in the semiconductor. Thus, in the evaluation apparatus 1 configured as above, crystalline quality of the semiconductor can be evaluated in such a manner that an intensity of the reflected microwave from the sample 2 is detected by the detector 18, and then analyzed by the personal computer 19. In addition, the detection (measurement) of the intensity of the reflected wave can be performed in a nondestructive and noncontact manner within a significantly short period of time. As for the detection, the personal computer 19 may be configured to perform a mapping measurement for determining crystalline quality in a predetermined area of the sample 2, by controlling a position of the stage 16 comprising an X-Y table.

Figure 2B:
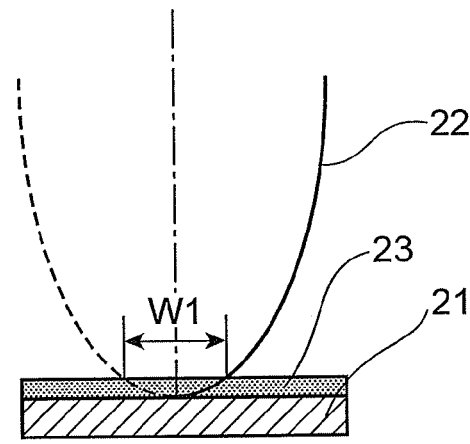
Figure 2C:
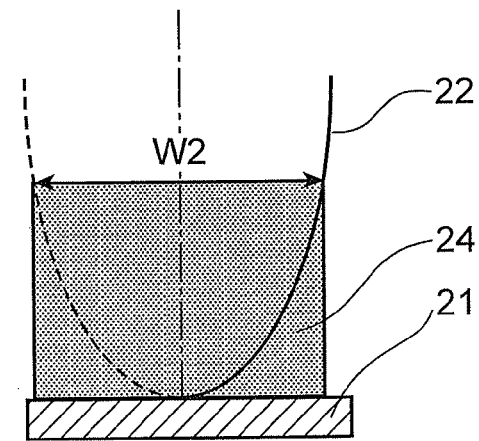

Meanwhile, as illustrated in FIG. 2(A), when a microwave is emitted to irradiate a surface 21a of a metal stage 21, a standing wave having a node on the surface 21a is formed, as indicated by the reference numeral 22. Thus, as illustrated in FIG. 2(B), when a thin sample 23 is placed on the metal sample 21, an electric field amplitude W1 of a standing wave on a surface of the metal sample 21 is small, so that an interaction with photo-excited carriers becomes weak, and the detection becomes substantially impossible due to a low signal intensity. On the other hand, as illustrated in FIG. 2(C), in a thick sample 24 (an optimal value of a thickness of the sample is $\lambda/4$, where $\lambda$ is a wavelength of the microwave), a relatively large electric field amplitude W2 is obtained, so that a resulting signal becomes strong. That is, the electric field amplitude W2 in the relatively thick sample 24 becomes greater than the electric field amplitude W1 in a relatively thin sample 23, and provides a stronger signal.

Therefore, in the first embodiment, when crystalline quality of a sample 2 is evaluated using the μ-PCD technique, in a situation where the sample 2 has a thin-film semiconductor 2a formed on an electrically conductive film 2b, the measurement is performed under a condition that the dielectric 3 is superimposed on the thin-film semiconductor 2a of the sample 2. The dielectric 3 is transparent to the ultraviolet excitation light.

This configuration makes it possible to, when crystalline quality of a semiconductor is evaluated using the μ-PCD (microwave reflection photoconductivity decay) technique, allow the sample 2 which has been unable to be evaluated because of insufficient sensitivity due to the absence of the dielectric 3, to be evaluated in a highly sensitive manner, while preventing generation of photo-excited carriers by ultraviolet excitation light from being hindered by the dielectric 3. In addition, between a microwave emission space and the sample 2, i.e., between air and silicon, a medium having an intermediate impedance (dielectric 3) is inserted, so that it becomes possible to avoid a rapid change in impedance against the microwave (to achieve impedance matching), thereby enhancing power transmission efficiency.

Assuming that a permittivity of the dielectric 3 is expressed in $\epsilon$, and a wavelength of the emitted electromagnetic wave is expressed in $\lambda$, a thickness d of the dielectric 3 is preferably set to satisfy the following formula (1):

$$d=\lambda/4(\epsilon)^{1/2} \tag{1}$$

Figure 3:
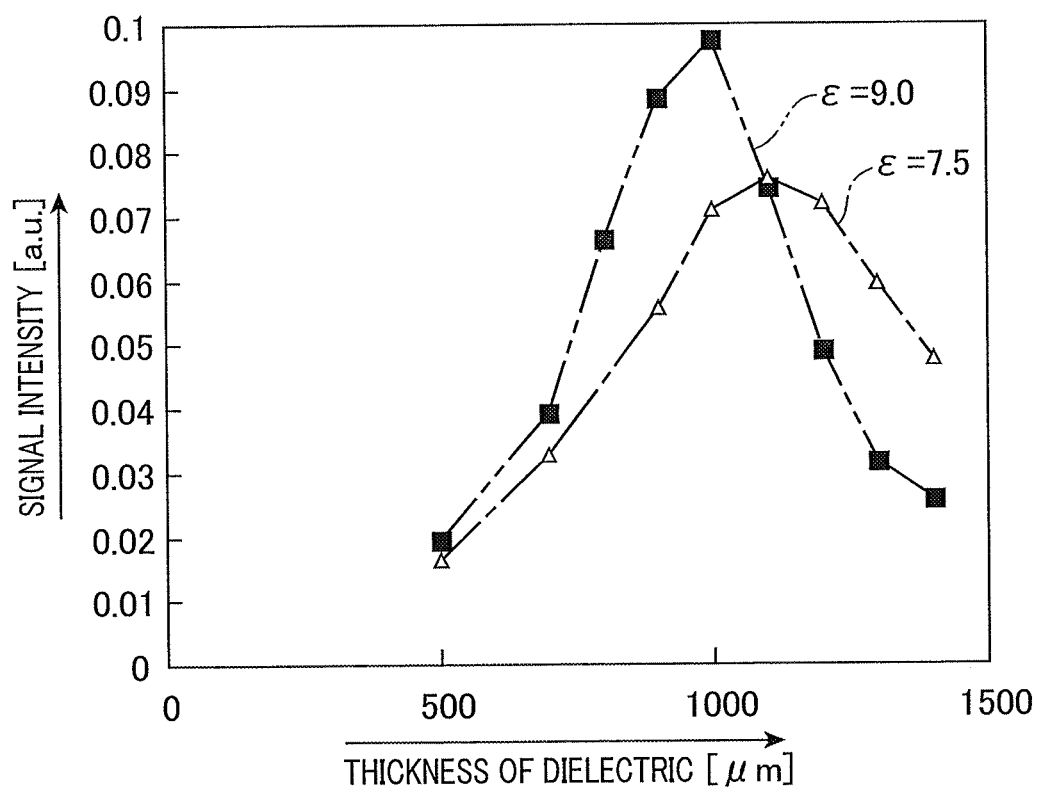
FIG. 3 is a graph illustrating a change in intensity of a reflected microwave occurring when a permittivity and a thickness of a dielectric which is used in the apparatus according to the first embodiment, wherein crystalline quality is evaluated from an intensity of a reflected wave of a microwave emitted to irradiate a sample.

FIG. 3 is a graph illustrating a change in intensity of a reflected microwave occurring when the permittivity and the thickness of the dielectric 3 which is used in the apparatus according to the first embodiment, wherein crystalline quality is evaluated from an intensity of a reflected wave of the microwave emitted to irradiate the sample 2. More specifically, a result of simulation conducted by the inventors of this application is illustrated in FIG. 3. This simulation was performed in two cases where the permittivity E of the dielectric 3 is set to 7.5 and 9.0 while setting the frequency of the microwave to 26 GHz. As seen from FIG. 3, when the thickness d of the dielectric 3 satisfies the above formula (1), the surface of the dielectric 3 is located at a position of an antinode of the amplitude of the reflected microwave, so that the sensitivity of the reflected microwave is maximized.

Figure 4:
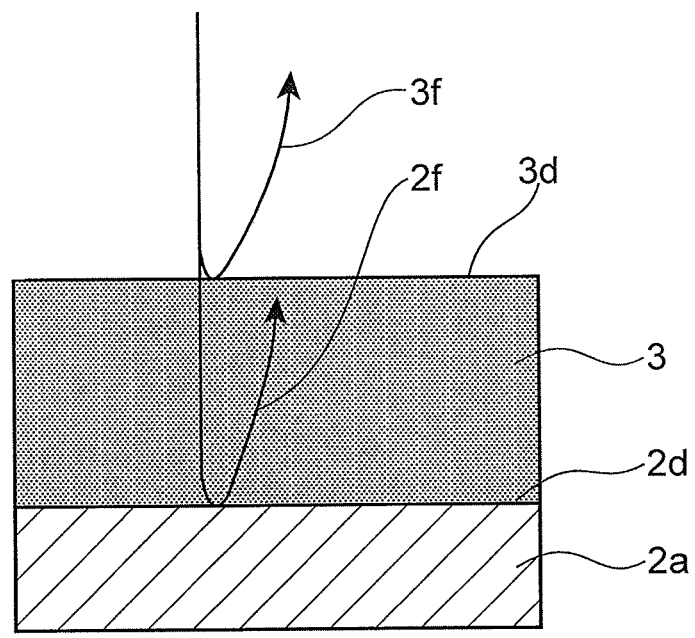
FIG. 4 is a diagram illustrating respective reflection states of a microwave by a surface of the sample and a surface of the dielectric.

In addition, when the above condition is satisfied, a microwave 3*f* reflected by a surface 3*d* of the dielectric 3 and a microwave 2*f* reflected by a surface 2*d* of the sample 2 have a relationship of a node and an anti-node, as illustrated in FIG. 4, so that they are canceled out. When the thickness d=$\lambda$/4n (n: refractive index), the reflection at the interfacial surface 3*d* of the dielectric 3 is minimized because the reflected wave at the interfacial surface 3*d* and the reflected wave from the interfacial surface 2*d* are mutually weakened by interference therebetween. In this condition, an energy transmittance (energy transmission efficiency) of the electromagnetic wave from air to the dielectric 3 is maximized, and consequently a greater electric field can be entered into an evaluation target film (thin-film semiconductor 2*a*), so that it becomes possible to increase a signal intensity.

As for the dielectric 3, although sensitivity is enhanced as the permittivity thereof becomes closer to a permittivity of the thin-film semiconductor 2*a* (e.g., in case of silicon, 11.7 to 11.8), it is necessary to use a dielectric free of absorption of ultraviolet excitation light, as mentioned above. Further, in order to allow the excitation light to be efficiently absorbed in the thin-film semiconductor 2*a*, it is preferable to select a wavelength of the ultraviolet excitation light source 17 to satisfy the following relation: a thickness of the thin-film semiconductor 2*a* <a length of penetration. Furthermore, in order to allow further highly-sensitive detection, the detector 18 may employ a differential antenna system.

Figure 5:
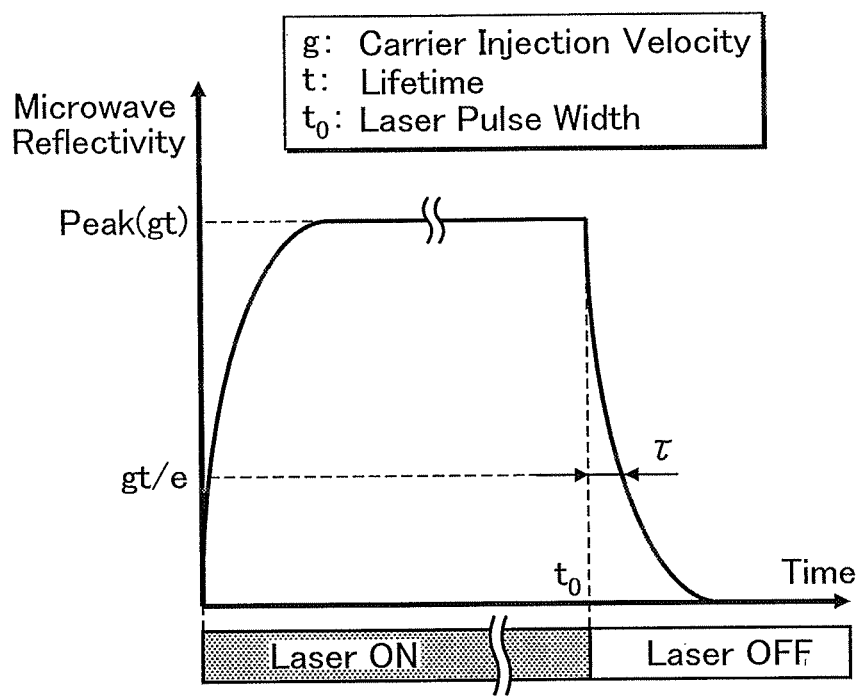
FIG. 5 is a graph illustrating a change in density of photo-excited carriers caused by excitation light emitted to irradiate a semiconductor.

The personal computer 19 as one example of the evaluation section is operable to evaluate the crystalline quality based on detecting a peak value Peak of the, intensity of the reflected electromagnetic wave by the detector 18 as one example of the detection section. This is based on the fact that a density of the photo-excited carriers caused by irradiation with the ultraviolet excitation light changes as illustrated in FIG. 5, and a carrier annihilation time becomes similar to the number of generated carriers when a lifetime $\tau$ of the photo-excited carriers is as short as n s or less (picosecond-order), as compared to a laser pulse irradiation time period t0. Upon start of the irradiation at Time t=0, the carrier density will be increased. Then, when a sufficient time exceeding the lifetime $\tau$ has elapsed, the number of carriers newly generated by irradiation with the excitation light and the number of carriers recombined and annihilated after the elapse of the lifetime $\tau$ balance out (counterbalance) each other, and the carrier density becomes constant. Subsequently, upon stop of the irradiation with the excitation light at Time t=t0, the carrier density will be reduced for the lifetime T.

More specifically, assuming that a carrier injection time (rate of generation of electron-hole pair by photoexcitation: per unit volume and unit time) is expressed in g, and the lifetime is also expressed in $\tau$ as with the above formula, a carrier density p in a semiconductor layer is derived by solving the following formula (2), and expressed as the following formula (3) under initial conditions: p=0, and t=0 (if it is desired to explicitly show that p is a function of time t, p may be described as p(t)):

$$dp/dt=g-p/\tau \tag{2}$$

$$p=g\tau(1-\exp(-t/\tau)) \tag{3}$$

Then, a peak value Peak of the carrier density p is a value at t=t0 which is an end timing of the laser pulse irradiation, and therefore can be expressed as the following formula (4):

$$\text{Peak}=g\tau(1-\exp(-t0/\tau)) \tag{4}$$

In this formula, $\tau \ll t0$, as mentioned above, and therefore Peak≈g$\tau$. Further, g is constant, and therefore the lifetime $\tau$ can be expressed as (approximated by) the following formula (5):

$$\tau \propto \text{Peak} \tag{5}$$

Thus, in the case where the lifetime $\tau$ is as short as n s or less (picosecond-order), it is difficult to measure the lifetime $\tau$ using a conventional low-cost measurement device. However, the use of the peak value as an evaluation value of crystalline quality instead of the lifetime $\tau$ makes it possible to evaluate the lifetime $\tau$ without using a high-cost measurement device.

In the first embodiment, the ultraviolet excitation light source 17 as one example of the excitation light emitting section is operable to emit excitation light intensity-modulated in predetermined periods, to irradiate the sample 2, and the personal computer 19 as one example of the evaluation section is operable to extract (detect) a periodic component synchronous with the intensity-modulation of the excitation light, from the intensity of the reflected electromagnetic wave detected by the detector 18 as one example of the detection section, and evaluate the crystalline quality of the sample based on the extracted detection signal intensity. This allows highly-sensitive measurement and evaluation. Particularly, in the case where the excitation light irradiation area is a small area, a change in intensity of the reflected electromagnetic wave is small and is therefore susceptible to noise. Even in this situation, based on the above modulated excitation and synchronized detection, an unwanted frequency component (noise) is optimally removed. In the first embodiment, a semiconductor laser can be used as the ultraviolet excitation light source 17. This is advantageous in view of not only a reduction in cost but also safety.

(Second Embodiment)

FIG. 6 is a block diagram illustrating a configuration of a thin-film semiconductor crystalline quality evaluation apparatus 31 according to a second embodiment of the present invention. The evaluation apparatus 31 according to the second embodiment is similar to the evaluation apparatus 1 according to the first embodiment. Thus, a corresponding element or component is defined by assigning the same reference numeral or code thereto, and its description will be omitted. In the evaluation apparatus 31, instead of the dielectric 3 in the first embodiment, a dielectric 33 is attached to a distal end of a waveguide 13, and the measurement is performed under a condition that a small distance d is defined between the dielectric 33 and a sample 2. For example, when a permittivity s of the dielectric 33 is 5.5, the small distance d is set to about 50 μm. That is, the small distance d is selectively set to the largest distance possible to an extent that an emitted microwave does not feel the small distance d (it exerts no influence on propagation).

Thus, the presence of the small distance d makes it possible to perform the evaluation in fully noncontact relation to the sample 2. The dielectric 33 may be formed in a size of the waveguide 13 to which the dielectric 33 is attached, i.e., a size which is different from, or less than, an overall size of the sample 2. In this case, it becomes possible to reduce a flexure thereof, thereby reducing the small distance d.

As above, this specification discloses techniques according to various aspects. Among them, major techniques will be outlined below.

According to one aspect, there is provided a crystalline quality evaluation apparatus for thin-film semiconductors, which comprises: an excitation light emitting section for emitting excitation light having energy equal to or greater than a band gap of a thin-film semiconductor of a sample, to irradiate a measurement site of the sample; an electromagnetic wave emitting section for emitting an electromagnetic wave to irradiate an irradiation position of the excitation light; a detection section for detecting an intensity of a reflected electromagnetic wave from the sample, which changes in response to irradiation with the excitation light; and an evaluation section for, based on a result of the detection by the detection section, evaluating crystalline quality of the sample, wherein the thin-film semiconductor of the sample is formed on an electrically conductive film, and wherein the crystalline quality evaluation apparatus further comprises a dielectric which is disposed between the sample and the electromagnetic wave emitting section, and transparent to the excitation light.

According to another aspect, there is provided a crystalline quality evaluation method for thin-film semiconductors, which comprises: emitting excitation light having energy equal to or greater than a band gap of a thin-film semiconductor of a sample, to irradiate a measurement site of the sample; in conjunction with the irradiation with the excitation light, emitting an electromagnetic wave to irradiate an irradiation position of the excitation light; detecting an intensity of a reflected electromagnetic wave from the sample, which changes in response to irradiation with the excitation light; and, based on a result of the detection, evaluating crystalline quality of the sample, wherein the thin-film semiconductor of the sample is formed on an electrically conductive film, and wherein the crystalline quality evaluation method further comprises disposing a dielectric transparent to the excitation light, between the sample and the electromagnetic wave emitting section.

In a semiconductor crystalline quality evaluation apparatus and method designed to evaluate crystalline quality of a semiconductor using a so-called μ-PCD technique, excitation light having energy equal to or greater than a band gap of a semiconductor of a sample is emitted to irradiate a measurement site of the sample, and concurrently an electromagnetic wave is emitted to irradiate an irradiation position of the excitation light. Then, an intensity of a reflected electromagnetic wave from the sample, which changes in response to irradiation with the excitation light, is detected, and crystalline quality of the sample is evaluated based on a result of the detection. In the case where the semiconductor of the sample is a thin-film semiconductor which is formed on an electrically conductive film, a dielectric transparent to the excitation light is disposed between the sample and the electromagnetic wave emitting section.

In the apparatus and method, when the semiconductor is irradiated with excitation light having energy equal to or greater than a band gap thereof, photo-excited carriers are generated in the semiconductor, wherein the photo-excited carriers move (migrate) according to an electric field of the electromagnetic wave. A state of the movement is influenced by the presence of impurities, defects or the like in the sample. Thus, an intensity of a reflected wave of the electromagnetic wave emitted to irradiate the semiconductor sample (a change in intensity of the reflected wave as compared to the emitted wave) can serve as an index of crystalline quality of the sample. In addition, this detection (measurement) of the intensity of the reflected wave can be performed within a significantly short period of time, in a nondestructive and noncontact manner. In the case of using the μ-PCD technique, when a microwave is emitted to irradiate a surface of a metal stage, a standing wave having a node on the surface is formed. Thus, when a thin sample is placed on the stage, an electric field amplitude of a standing wave on a surface of the sample is small, so that an interaction with photo-excited carriers becomes weak, and a signal intensity becomes lowed. On the other hand, when a thick sample is placed on the stage (an optimal value of a thickness of the sample is λ/4), a relatively large electric field amplitude is obtained, so that a resulting signal becomes strong.

Therefore, in the above crystalline quality evaluation apparatus and method, in a situation where the semiconductor is a thin film, and the thin-film semiconductor is formed on an electrically conductive film, as in a bottom electrode of a solar cell or the like, a dielectric transparent to the excitation light is disposed between the thin-film semiconductor of the sample and the electromagnetic wave emitting section. This makes it possible to allow a sample which has been unable to be evaluated because of insufficient sensitivity due to the absence of the dielectric, to be also evaluated in a highly sensitive manner, while preventing generation of photo-excited carriers by ultraviolet excitation light from being hindered.

In addition, between a microwave emission space and the sample, i.e., between air and silicon, the dielectric as a medium having an intermediate impedance is inserted, so that it becomes possible to avoid a rapid change in impedance against the electromagnetic wave (to achieve impedance matching), thereby enhancing power transmission efficiency.

In one preferred embodiment, the crystalline quality evaluation apparatus satisfies the following relation: $d=\lambda/4(\in)^{1/2}$, where: $\in$ is a permittivity of the dielectric; d is a thickness of the dielectric; and λ is a wavelength of the emitted electromagnetic wave.

The crystalline quality evaluation apparatus configured in this manner can maximize efficiency of power transmission to the thin-film semiconductor.

In another preferred embodiment of the crystalline quality evaluation apparatus, the evaluation section is operable to evaluate the crystalline quality based on detecting a peak value of the intensity of the reflected electromagnetic wave by the detection section.

In the above crystalline quality evaluation apparatus, when a lifetime τ of the photo-excited carriers is as short as n s or less (picosecond-order), it is difficult to measure the lifetime τ using a conventional low-cost measurement device. However, when excitation pulse width >> lifetime τ, the lifetime τ has the following relation: τ∝ peak value (becomes similar to the peak value)

Thus, in the crystalline quality evaluation apparatus configured as above, the peak value is used as an evaluation value of crystalline quality instead of the lifetime τ, so that it becomes possible to evaluate the lifetime τ without using a high-cost measurement device.

In yet another preferred embodiment of the crystalline quality evaluation apparatus, the dielectric is disposed above the sample with a small distance therebetween.

The crystalline quality evaluation apparatus configured in this manner can perform the evaluation in fully noncontact relation to the sample.

In still another preferred embodiment of the crystalline quality evaluation apparatus, the electromagnetic wave emitting section includes a waveguide for guiding the electromagnetic wave to the excitation light irradiation position, wherein the dielectric is attached to a distal end of the waveguide of the electromagnetic wave emitting section.

In the crystalline quality evaluation apparatus configured in this manner, the dielectric may be formed in a size of the waveguide to which the dielectric is attached, i.e., a size which is different from, or less than, an overall size of the sample. In this case, it becomes possible to reduce a flexure thereof, thereby reducing the small distance.

In yet still another preferred embodiment of the crystalline quality evaluation apparatus, the excitation light emitting section is operable to emit excitation light intensity-modulated in predetermined periods, to irradiate the sample, and the evaluation section is operable to extract a periodic component synchronous with the intensity-modulation of the excitation light, from the intensity of the reflected electromagnetic wave detected by the detection section, and evaluate the crystalline quality of the sample based on the extracted detection signal intensity.

In the crystalline quality evaluation apparatus configured in this manner, highly-sensitive measurement and evaluation can be achieved based on the modulated excitation and synchronized detection as in the Patent Document 1. Particularly, in the case where the excitation light irradiation area is a small area, a change in intensity of the reflected electromagnetic wave is small and is therefore susceptible to noise. Even in this situation, based on the above modulated excitation and synchronized detection, an unwanted frequency component (noise) can be optimally removed.

This application is based on Japanese Patent Application Serial No. 2010-211524 filed in Japan Patent Office on Sep. 22, 2010, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

Industrial Applicability

The present invention can provide a crystalline quality evaluation apparatus and method for evaluating crystalline quality of a thin-film semiconductor.

What is claimed is:

1. A crystalline quality evaluation apparatus for thin-film semiconductors, comprising:

an excitation light emitting section for emitting excitation light having energy equal to or greater than a band gap of a thin-film semiconductor of a sample, to irradiate a measurement site of the sample;

an electromagnetic wave emitting section for emitting an electromagnetic wave to irradiate an irradiation position of the excitation light;

a detection section for detecting an intensity of a reflected electromagnetic wave from the sample, which changes in response to irradiation with the excitation light;

an evaluation section for, based on a result of the detection by the detection section, evaluating crystalline quality of the sample; and a dielectric which is disposed between the sample and the electromagnetic wave emitting section, and transparent to the excitation light, wherein the thin-film semiconductor of the sample is formed on an electrically conductive film, and wherein the crystalline quality evaluation apparatus further satisfies the following relation: $d=\lambda/4(\in)^{1/2}$, where: $\in$ is a permittivity of the dielectric; d is a thickness of the dielectric; and λ is a wavelength of the emitted electromagnetic wave.

2. The crystalline quality evaluation apparatus according to claim 1, wherein the evaluation section is operable to evaluate the crystalline quality based on detecting a peak value of the intensity of the reflected electromagnetic wave by the detection section.

3. The crystalline quality evaluation apparatus according to claim 1, wherein:

the excitation light emitting section is operable to emit excitation light intensity-modulated in predetermined periods, to irradiate the sample; and the evaluation section is operable to extract a periodic component synchronous with the intensity-modulation of the excitation light, from the intensity of the reflected electromagnetic wave detected by the detection section, and evaluate the crystalline quality of the sample based on the extracted detection signal intensity.

4. The crystalline quality evaluation apparatus according to claim 1, wherein the dielectric is disposed above the sample with a small distance therebetween.

5. The crystalline quality evaluation apparatus according to claim 4, wherein the electromagnetic wave emitting section includes a waveguide for guiding the electromagnetic wave to the excitation light irradiation position, and wherein the dielectric is attached to a distal end of the waveguide of the electromagnetic wave emitting section.

6. A crystalline quality evaluation method for thin-film semiconductors, comprising:

emitting excitation light having energy equal to or greater than a band gap of a thin-film semiconductor of a sample, to irradiate a measurement site of the sample;

in conjunction with the irradiation with the excitation light, emitting an electromagnetic wave to irradiate an irradiation position of the excitation light;

detecting an intensity of a reflected electromagnetic wave from the sample, which changes in response to irradiation with the excitation light;

based on a result of the detection, evaluating crystalline quality of the sample; and disposing a dielectric transparent to the excitation light, between the sample and the electromagnetic wave emitting section, wherein the thin-film semiconductor of the sample is formed on an electrically conductive film, and wherein the crystalline quality evaluation method satisfies the following relation: $d = \lambda/4(\in)^{1/2}$, where: $\in$ is a permittivity of the dielectric; d is a thickness of the dielectric; and $\lambda$ is a wavelength of the emitted electromagnetic wave.

* * * * *